(12) United States Patent
Smith et al.

(10) Patent No.: US 7,468,411 B2
(45) Date of Patent: *Dec. 23, 2008

(54) THERMOPLASTIC ELASTOMER COMPOSITIONS CONTAINING A PHASE CHANGE SOLVENT AND SELECTED PROCESSING OILS

(75) Inventors: Steven Daryl Smith, Fairfield, OH (US); Mark William Hamersky, Hamilton, OH (US); Amy Elizabeth Eichstadt, Beaver Creek, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/769,344

(22) Filed: Jan. 30, 2004

(65) Prior Publication Data

US 2004/0220304 A1    Nov. 4, 2004

Related U.S. Application Data

(63) Continuation-in-part of application No. 10/429,531, filed on May 5, 2003.

(60) Provisional application No. 60/399,963.

(51) Int. Cl.
C08K 5/00 (2006.01)

(52) U.S. Cl. .................. 524/219; 524/239; 524/294; 524/296; 524/297; 524/298

(58) Field of Classification Search .............. 524/294, 524/296, 297, 298, 219, 239
See application file for complete search history.

(56) References Cited

U.S. PATENT DOCUMENTS

| | | | |
|---|---|---|---|
| 2,075,107 A | | 3/1937 | Frazier |
| 2,453,264 A | | 11/1948 | Rehberg |
| 2,777,871 A | | 1/1957 | Strain |
| 3,376,275 A | | 4/1968 | Bayerlein et al. |
| 3,562,356 A | | 2/1971 | Nyberg et al. |
| 3,734,891 A | | 5/1973 | Knopka |
| 3,755,231 A | | 8/1973 | Muir et al. |
| 3,981,838 A | * | 9/1976 | Wilson .................. 524/295 |
| 4,098,751 A | | 7/1978 | Mark et al. |
| 4,123,413 A | | 10/1978 | Mark et al. |
| 4,131,581 A | | 12/1978 | Coker |
| 4,146,522 A | | 3/1979 | Heckles |
| 4,210,568 A | | 7/1980 | Makowski et al. |
| 4,293,473 A | | 10/1981 | Eastman |
| 4,387,214 A | | 6/1983 | Passmore et al. |
| 4,442,270 A | | 4/1984 | Passmore et al. |
| 4,500,662 A | | 2/1985 | Lai |
| 4,578,302 A | | 3/1986 | Schmidt, Jr. et al. |
| 4,618,630 A | * | 10/1986 | Knobel et al. ............. 521/105 |
| 4,704,110 A | | 11/1987 | Raykovitz et al. |
| 4,738,807 A | | 4/1988 | Aitken et al. |
| 4,745,026 A | | 5/1988 | Tsukahara et al. |
| 4,882,375 A | | 11/1989 | Tyrell et al. |
| 5,352,531 A | | 10/1994 | Roberts et al. |
| 5,389,711 A | * | 2/1995 | Westbrook et al. ......... 524/288 |
| 5,418,281 A | | 5/1995 | Yung et al. |
| 5,503,919 A | | 4/1996 | Litchholt et al. |
| 5,534,303 A | | 7/1996 | Roberts et al. |
| 5,534,583 A | | 7/1996 | Roberts et al. |
| 5,540,983 A | | 7/1996 | Maris et al. |
| 5,580,916 A | | 12/1996 | Traverso et al. |
| 5,624,986 A | | 4/1997 | Bunnelle et al. |
| 5,627,229 A | | 5/1997 | Bunnelle et al. |
| 5,633,319 A | | 5/1997 | Silvi et al. |
| 5,714,254 A | | 2/1998 | Jacob |
| 5,853,874 A | | 12/1998 | Jacob |
| 5,910,527 A | | 6/1999 | Alper et al. |
| 5,939,483 A | | 8/1999 | Kueppers |
| 5,945,485 A | | 8/1999 | Struglinski et al. |
| 6,080,480 A | | 6/2000 | Shiba et al. |
| 6,117,176 A | | 9/2000 | Chen |
| 6,177,508 B1 | | 1/2001 | Ohmori et al. |

(Continued)

FOREIGN PATENT DOCUMENTS

EP    0 044 675 B1    5/1984

(Continued)

OTHER PUBLICATIONS

Chem. Abstracts 1996:310113, "End-grafting oligoesters based on terephthalic acid and linear diols for high solids coatings", Teng et al., Journal of Applied Polymer Science (1996) 60(10), 1609-1618.

(Continued)

*Primary Examiner*—Peter D Mulcahy
(74) *Attorney, Agent, or Firm*—Angela Marie Stone; Julie A. McConihay; Jay A. Krebs

(57) ABSTRACT

Novel elastomeric compositions which contain at least one thermoplastic elastomer and at least one phase change solvent and at least one processing oil. The presence of particular processing oils, e.g., poly(alphaolefins), provide a means to increase mechanical properties compared to commercially available mineral oils. The oils of the present invention are chosen as to minimize the depression of glass transition temperature of the hard-block of the thermoplastic elastomer. The phase change behavior of these materials produce elastomeric compositions that exhibit lowered viscosity and lowered processing temperature without substantially compromising the mechanical properties of the elastomeric composition.

19 Claims, 2 Drawing Sheets

U.S. PATENT DOCUMENTS

| | | |
|---|---|---|
| 6,187,425 B1 | 2/2001 | Bell et al. |
| 6,703,115 B2 | 3/2004 | Hale et al. |
| 6,723,444 B2 | 4/2004 | Kobayashi et al. |

FOREIGN PATENT DOCUMENTS

| | | |
|---|---|---|
| EP | 0 277 750 A2 | 2/1988 |
| EP | 0 989 162 A1 | 3/2000 |
| EP | 1 193 284 A1 | 4/2002 |
| FR | 2 488 266 A1 | 2/1982 |
| GB | 849086 | 9/1960 |
| GB | 1181807 | 2/1970 |
| GB | 1190417 | 5/1970 |
| GB | 1193626 | 6/1970 |
| GB | 1193627 | 6/1970 |
| JP | 2189348 | 7/1990 |
| JP | 2196844 A | 8/1990 |
| JP | 5125240 A | 5/1993 |
| WO | WO 96/05253 | 2/1996 |
| WO | WO 00/11092 A1 | 3/2000 |

OTHER PUBLICATIONS

Chem. Abstracts 1992:21832, "Liquid-crystalline oligoesters containing single-ringaromatic units separated by aliphatic spacers", Teng et al., Polymeric Materials Science and Engineering (1991), 65, 33-4.

Chem. Abstracts 1995:976847, "A test of the applicability of small-molecule group additivity parameters in the estimation of fusion entropies of macromolecules", Chickos et al., Thermochimica Acta (1995), 264, 13-26.

* cited by examiner

THERMOPLASTIC ELASTOMER COMPOSITIONS CONTAINING A PHASE CHANGE SOLVENT AND SELECTED PROCESSING OILS

CROSS-REFERENCE TO RELATED APPLICATION

This application is a continuation-in-part of U.S. application Ser. No. 10/429,531, filed May 5, 2003, which claims the benefit of U.S. Provisional Application 60/399,963, filed Jul. 31, 2002.

FIELD OF INVENTION

The present invention relates to novel elastomeric compositions containing phase change solvents and selected processing oils or processing oil compositions. The presence of the selected processing oil improves mechanical properties over conventional oils, such as mineral oil. The phase change behavior of these agents produce elastomeric compositions that exhibit lowered viscosity and lowered processing temperature without substantially compromising the mechanical properties. The present invention also relates a method of lowering the viscosity and improving the processability of a thermoplastic elastomer using the phase change solvent and the selected processing oils.

BACKGROUND

Elastomeric materials are traditionally produced through extrusion processes to make sheets or strands of elastomeric materials. Subsequent cutting of the elastomeric sheets or stands to the desired size and/or shape and joining the cut pieces to a substrate are typically required. Overall, the above processes involve multiple steps to produce the finished product and may generate much wasted materials. In view of these drawbacks, the ability to print or spray elastomeric compositions is particularly advantageous. The printing and spraying processes may deliver the elastomeric materials directly onto the substrate, thus, avoid the drawback of a multi-step process. These processes may also deliver the elastomeric materials only to targeted areas where elastic properties are needed, thus, minimize the amount of waste generated. Moreover, these processes may also provide controlled delivery of varying amounts of elastomeric materials to discrete areas in a single step, which is difficult, if not impossible to achieve by traditional extrusion/molding processes.

Fiber spinning, melt blowing, and other processes require low melt viscosity materials, which are typically thermoplastic polymers such as polyethylene, polypropylene, polyesters, and polyamides. Elastomeric materials having suitably low melt viscosity for these processes are olefinic elastomers made from single site catalysts. Many elastomeric materials, such as styrenic block copolymer compositions, are generally considered not suitable for such low viscosity processes. The discoveries by the present inventors have made the elastomeric compositions of the present invention uniquely suitable for these low melt viscosity processes.

It is well known that plasticizers, viscosity modifiers and processing oils may be used to lower the viscosity and improve the melt processability of TPE's or mixtures. However, due to their low molecular weight and their softness and/or fluidity down to room temperature, these agents tend to reduce the mechanical properties of the TPE's and blends. In contrast, the phase change solvents are solid-like at or below body temperature, thus, they may function like reinforcing particles (i.e., fillers) in the TPE's and blends. Moreover, the phase change solvents, due to their chemical formula and molecular weights, may be intimately mixed the TPE's and function like compatibilizers. When they solidify, they may be fairly homogeneously dispersed throughout the TPE matrix. Homogeneous distribution of reinforcing particles is desirable since few stress concentration spots (detrimental to mechanical properties) are created in such structures. Their compatibilizing function may also lead to reduced phase sizes and reduced stress concentrations at the interfaces between the phases of the TPE's.

Additionally, oils are added to reduce cost and further increase the process characteristics of polymeric materials. However, the addition of highly branched and low molecular weight oils is deleterious to mechanical properties.

Block copolymers comprising one or more alkenylarene polymer block and one or more olefinic polymer block are generally known as thermoplastic elastomers (TPE's). The block copolymers are elastomeric in the sense that they typically have a three-dimensional, entangled (alternatively known as "physically crosslinked") structure below the glass transition temperature ($T_g$) of the styrenic block such that they exhibit elastic memories in response to external forces. The block copolymers are thermoplastic in the sense that they can be softened or melted above the glass or crystalline transition temperature of the alkenylarene block, processed, and cooled/solidified several times with little or no change in physical properties (assuming a minimum of oxidative degradation).

These block copolymers are known to have high strength and elasticity at ambient temperatures. The high strength and elasticity of these block copolymers are due to the microphase separated network structure wherein the olefinic blocks and the alkenylarene blocks separate from structurally dissimilar blocks and entangle with structurally similar blocks to form separate domains. The olefinic blocks typically have a glass transition temperature below ambient temperature, thus, they are relatively free to move about and form the soft, rubbery phase at or above ambient temperature. In contrast, the alkenylarene blocks have a glass and/or crystalline transition temperature above ambient temperature, thus, they are relatively immobilized in the entangled state and form the hard phase. However, at body temperature, the copolymers may begin to lose their mechanical properties after some time. The deterioration of properties appears to be associated with the copolymer movements, especially the movements of the alkenylarene blocks. At body temperature, sometimes accompanied with tension or load, the previously immobile alkenylarene blocks begin to slip pass neighboring alkenylarene blocks. Since the alkenylarene blocks form the hard phases, which are primarily responsible for the mechanical properties, such motions of the alkenylarene blocks adversely affect the mechanical properties of the copolymer. The relative hardness of the alkenylarene blocks can be assessed by the value of a measured glass transition temperature. A high glass transition temperature indicates strong interactions and restricted motion of the styrenic chains, which ultimately leads to tensile strength. Conversely, low glass transition temperatures indicate the motion of molecules can occur easier and causes a drop in tensile performance.

Plasticizers or processing oils are often added to the block copolymers to lower the viscosity and improve the processability of the block copolymers. Other polymers may also be added to compatibilize the blends and/or improve the mechanical properties. Blends comprising block copolymers are described in U.S. Pat. Nos. 3,562,356 (Nyberg et al.);

4,704,110 (Raykovitz et al.); 4,578,302 (Schmidt et al.); 5,503,919 (Litchholt, et al.); 5,540,983 (Maris et al.); 6,117,176 (Chen); and 6,187,425 (Bell et al.).

However, the addition of the plasticizers and/or some processing oils lower the strength and elastic properties of the block copolymer compositions. Such oils often contain a high degree of branching, low molecular weights, and polar functionalities. The degree of branching and low molecular weights contributes to reduced glass transition temperatures and changing the relaxation times of the hard phase within the thermoplastic elastomer. The alteration of the glass transition temperature and molecular relaxation times are well-known to affect viscoelastic properties.

Therefore, it is desirable to provide a novel combination of materials that reduces the viscosity and improves the processability of block copolymer compositions without substantially compromising their mechanical properties.

It is also desirable to provide a material that exhibits a phase change as the temperature is raised and/or lowered such that the novel material effects very sharp changes in the characteristics (e.g., viscosity) of the block copolymer compositions at or around the phase change temperature of the material.

Moreover, it is desirable that the viscosity of the phase change solvent and of its block copolymer blends can be varied over a broad range to achieve the suitable viscosity for different fabricating processes, such as extrusion, injection molding, melt spinning, blow molding, spraying, printing, coating, and the like.

SUMMARY OF THE INVENTION

The present invention relates to elastomeric compositions containing phase change solvents and processing oils that do not negatively affect the mechanical properties. The compositions may comprise:
  a) a thermoplastic elastomer which is a block copolymer having at least one soft block and at least one hard block;
  b) a phase change solvent having the general formula:

  (I)

  (II)

  (III)

  (IV)

  (V)

a mixture thereof;
  wherein Q may be a substituted or unsubstituted difunctional aromatic moiety; P is $CH_2$; R and R' are the same or different and are independently selected from H, $CH_3$, COOH, $CONHR_1$, $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 2 to 7; a processing oil or processing oil composition producing a glass transition temperature of greater than about 85° C. for polystyrene homopolymer.

The processing oil may preferably be a poly (α-olefins), with 4-18 carbons, or mixtures of synthetic oils and mineral oils. The composition may also comprise a nucleating agent or thermoplastic polymer if desired.

Typically, the phase change solvent has a phase change in a temperature range from about 40° C. to about 250° C. The processing oils do not plasticize polystyrene to a large extent, which leads to resulting compositions that exhibit low viscosities, low processing temperatures, and good mechanical properties. The elastomeric composition may be processed by various methods, including extrusion, injection molding, melt spinning, blow molding, printing, spraying, coating, and the like.

The present invention also relates a method of lowering the viscosity and improving the processability of a thermoplastic elastomer using the phase change solvent and processing oil.

DETAILED DESCRIPTION OF THE INVENTION

Figure 1:
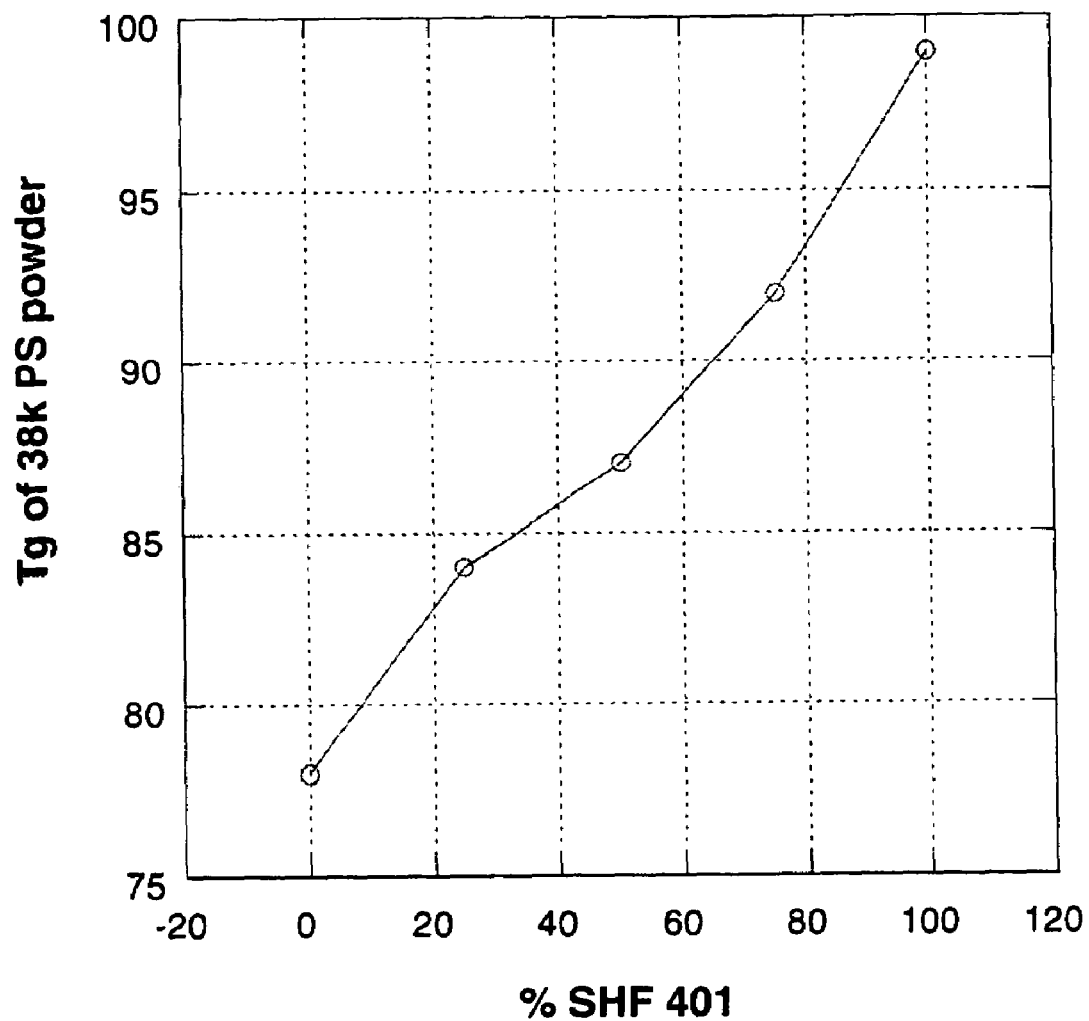
FIG. 1 is a plot of the glass transition temperatures produced for a polystyrene homopolymer in the presence of a variety of processing oil compositions.

As used herein, the terms "elastic" or "elastomeric" refer to any material which is capable of being elongated or deformed to at least 200% of its original dimension under an externally applied force, and which will substantially resume its original dimension, sustaining only small permanent set (typically no more than about 20%), after the external force is released. The term "elastomer" refers to any material exhibiting elastic properties as described herein above.

As used herein, the term "thermoplastic" refers to any material which can be melted and re-solidified with little or no change in physical properties (assuming a minimum of oxidative degradation).

As used herein, the term "AA ratio" refers to ratio between the number of aliphatic carbons in the P units to the number of aromatic carbons in the Q units of the phase change solvent, wherein the aromatic carbons of the Q units exclude those carbons that may be present in the substituents. This definition has been described thoroughly in U.S. patent application Ser. No. 10/429,531 to Smith et al., filed May 5, 2003.

As used herein, the term "percent elongation" refers to the ratio obtained from dividing the length of the sample material measured at a specific condition (e.g., while the sample material is elongated under an applied force) by the length of the sample material in its undeformed state, then multiplied by 100. Thus, a sample material in its undeformed or unstrained state has a 100% elongation.

As used herein, the term "percent strain" refers to the difference between the length of the sample material measured at a certain elongation and the length of the samples material in its undeformed state, divided by the length of the sample material in its undeformed state, then multiplied by 100. Thus, a sample material in its undeformed or unstrained state has a 0% strain.

As used herein, the term "stress relaxation" or "force relaxation" refers to the percentage loss of load (i.e., tension force) between the maximum load encountered after elongating a sample material at a specific rate of strain to a predetermined length and the remaining load measured after the sample material has been held at that length for a specified period of time. Stress relaxation is expressed as percentage loss of the initial load after a specific period of time at a specific strain of a sample material.

All percentages, ratios and proportions used herein are defined by weight of the composition unless otherwise specified.

Processing Oils

The present inventors have found that particular processing oils, particularly synthetic oils such as polymers and/or oligomers of diene type monomers, which include materials such as poly($\alpha$-olefins) (PAOs) offer significant advantages over conventional mineral oils. The synthetic oils can be used alone or in composition with a natural oil such as mineral oil. The processing oil or processing oil composition must produce a glass transition temperature of greater than about 85° C. for a polystyrene homopolymer. Preferably, the glass transition temperature produced for polystyrene will be greater than 87° C. and more preferably greater than 90° C. The processing oil can be a synthetic oil, a combination of synthetic oils, or a combination of synthetic and natural oils. The processing oil described in this invention can be either a naturally produced or available oil, such as mineral oils, paraffin oils, isoparaffinic oils, naptha oils, petrolatum, waxes or mixtures thereof, or wholly synthetic oils, such as poly(alpha olefins) synthesized from butene, hexane, octane, decene, and dodecene monomers. The poly(alpha olefin) can be a polydodecene, polydecene, polyoctene, polybutylene, polybutene, olefinic oligomers, or any combination thereof. More specifically, the poly(alpha olefin) can be a poly(1-decene), poly(1-dodecene), poly(1-octene), or any combination thereof. EPR rubber with a molecular weight of 2000 and C10 with molecular weights from 700 to 2000 are also suitable processing oils. If a combination of synthetic and natural oils is used, preferably, the synthetic oil comprises at least about 40% and more preferably greater than about 45% by weight of the processing oil composition. The processing oil mixture may contain greater than about 50% of a synthetic oil depending upon the specific synthetic oil used. Any combination of oils and percentage of oils is suitable for the present invention as long as the glass transition temperature produced for a polystyrene homopolymer is greater than about 85° C. For example, for SHF 401, a mixture of this synthetic oil with mineral oil would optimally include greater than about 35% SHF 401.

Although very similar in chemical make-up, there are some subtle but important differences between mineral and synthetic oils. For example, synthetic oils can be made with specific monomers such as 1-decene or 1-octene that provide an overall reduction in "branching content" of the oil which greatly affects the oils' ability to blend and intimately mix with the rubber phase while not plasticize the hard phase of the thermoplastic elastomer. Another feature that synthetic oils offer is the wide range of molecular weights, especially the upper limit. Typical mineral oils are limited by distillation processes which become cost prohibitive as the boiling points of the material increase. However, synthetic oils can be made with specific molecular weights that far surpass the commercially available mineral oils. For example, the synthetic oil Durasyn 180 (BP-Amoco Chemicals) has a molecular weight of 2000 g/mol, whereas the mineral oil Drakeol 600 (Penreco Co.) has a molecular weight of 700 g/mol. Although any molecular weight is suitable, the molecule weight of the processing oil is typically from about 500 to about 3000 g/mol, preferably from about 700 to about 2500 g/mol and more preferably from about 1000 to about 2200 g/mol. Additionally, the molecular weight distribution can be altered to prepare oils very broad or fairly narrow in the dispersity of chain length. Taken together, the branching content, molecular weight and distribution available with synthetic oils provides significant opportunities and advantages over mineral oils to improve tensile properties with little effect to Theological properties. As the data shown in the examples and figures indicate, the use of synthetic oils provides unexpected benefits in tensile strength and long time force relaxation. The oil may possess sufficient molecular weight and chemical structure to enhance or at least maintain properties of the elastomer.

The processing oil or processing oil composition is typically present in an amount of from about 1% to about 70% by weight of the composition. Preferably, the processing oil is present in an amount of from about 5% to about 50%. The oils of the present invention are chosen as to minimize the depression of glass transition temperature of the hard-block of the thermoplastic elastomer. The phase change behavior of these materials produce elastomeric compositions that exhibit lowered viscosity and lowered processing temperature without substantially compromising the mechanical properties of the elastomeric composition.

Thermoplastic Elastomer: Block Copolymer

Block copolymers of the present invention have at least one hard block and at least one soft block. The copolymers have one or more alkenylarene polymer blocks (the hard block) and one or more olefinic polymer blocks (the soft block). The block copolymers are elastomeric in the sense that they typically have a three-dimensional, entangled (alternatively known as "physically crosslinked") structure below the glass transition temperature ($T_g$) of the alkenylarene block such that they exhibit elastic memories in response to external forces. The block copolymers are thermoplastic in the sense that they can be softened or melted above the glass or crystalline transition temperature of the alkenylarene block, processed, and cooled/solidified several times with little or no change in physical properties (assuming a minimum of oxidative degradation). The alkenylarene block is derived from monomers such as styrene, alpha-methyl styrene, vinyl toluene, para-methyl styrene, other alkyl styrene derivatives, or mixtures thereof, or a copolymer derived from alkenylarene monomers and short C2-C6 alkene monomers such as ethylenes, propylenes, butylenes; C2-C6 diene monomers such as isoprenes, butadienes; or mixtures of alkene/diene monomers. The olefinic block may be a diene polymer derived from unsaturated or partially saturated diene monomers of from about 4 to about 6 carbons. Suitable diene monomers may include butadiene, isoprene, and the like. The olefinic block may also be an olefinic polymer derived from linear or branched alkene monomers of from about 2 to about 6 carbon atoms. Suitable alkene monomers may include ethylene, propylene, butylene, isoprene, and mixtures thereof. The olefinic block may also comprise a combination of the above monomers, such as ethylene/propylene polymers, ethylene/butylene polymers, and the like.

A preferred block copolymer is a styrene-olefine-styrene triblock copolymer selected from the group consisting of styrene-butadiene-styrene, styrene-ethylene/butylenes-styrene, styrene-ethylene/propylene-styrene, styrene-isoprene-styrene, hydrogenated polystyrene-isoprene/butadiene-styrene, and combinations thereof. The block copolymer is present in the composition in an amount of from about 1% to about 98% by weight of the composition. Preferably, the block copolymer is present in an amount of from about 10% to about 85%.

Phase Change Solvent

Phase change solvents have been described in U.S. patent application Ser. No. 10/429,531 to Smith et al., filed May 5, 2003. These phase change solvent materials are included in the examples of the current invention. Preferably, a phase change solvent will have the general formula:

$$R'\text{-}P_y\text{-}(Q\text{-}P_x)_{n-1}\text{-}Q\text{-}P_y\text{-}R; \quad (I)$$

$$R'\text{-}P_y\text{-}(Q\text{-}P_x)_n\text{-}R; \quad (II)$$

$$R'\text{-}(Q\text{-}P_x)_n\text{-}R; \quad (III)$$

$$R'\text{-}(Q\text{-}P_x)_{n-1}\text{-}Q\text{-}P_y\text{-}R; \quad (IV)$$

$$R'\text{-}(Q\text{-}P_x)_{n-1}\text{-}Q\text{-}R; \text{ or} \quad (V)$$

a mixture thereof;

wherein Q may be a substituted or unsubstituted difunctional aromatic moiety; P is $CH_2$; R and R' are the same or different and are independently selected from H, $CH_3$, COOH, $CONHR_1$, $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 2 to 7.

The phase change solvent will preferably have a phase change in a temperature range of from about 40 to about 250° C. The phase change solvent may exhibit at least one phase change which is a crystalline transition, a glass transition, or a liquid crystalline transition. The phase change solvent will preferably have a number-average molecular weight of from about 150 to about 5,000. The AA ratio of the phase change solvent will preferably range from about 0.25 to about 4.

The phase change solvent is typically present in the composition in an amount of from about 1% to about 70% by weight of the composition. Preferably, the phase change solvent is present in an amount of from about 5% to about 50%.

Optional Ingredients

Optionally, various thermoplastic polymers may be used in the present compositions in an amount from about 1% to about 50%, preferably from about 5% to about 40%, and more preferably from about 10% to about 30%, by weight of the composition. Suitable thermoplastic polymers may associate with the hard blocks of the block copolymers to form an entangled three-dimensional network. Thermoplastic polymers such as polyphenylene oxide, and alkenylarene resins derived from monomers including styrene, alpha-methyl styrene, other styrene derivatives, vinyl toluene, and mixtures thereof, are useful in the present invention. The thermoplastic polymers, such as polystyrene, poly(alpha-methyl styrene), polyphenylene oxide, polyolefins, and mixtures thereof, are suitable because they are chemically compatible with the styrenic hard blocks of the block copolymer. Not intending to be bound by theory, it is believed to be advantageous to have compatible components in a composition so that the components may be intimately mixed to form an entangled three-dimensional network structure. This entangled network structure is believed to be capable of improving the mechanical properties, such as tensile, elastic and stress relaxation properties.

A nucleating agent can optionally be included in the compositions of the present invention. Generally, from about 0.01% to about 50% by weight of the composition is suitable. Preferably, the nucleating agent is present in an amount of from about 0.1% to about 5%. Not intending to be bound by theory, it is believed that a nucleating agent will help smaller crystals of phase change solvents to form and increase the crystallization or solidification rate of the composition Suitable nucleating agents include inorganic or polymeric materials including particulate materials such as talc, silica, carbon black, clay, metal oxides, metal carbonates, and mixtures thereof. Other nucleating agents include polymers having a molecular weight greater than about 5000.

Other additives may be incorporated into the present compositions including stabilizers and/or anti-oxidants, dyes, pigments, fillers, anti-blocking agents, flame retardants, and the like. The present compositions can optionally include a tackifying resin as many compositions of this type do. However, it has been found that a tackifying resin is not required for effectiveness of the present compositions.

Properties

The shear viscosity of the compositions, measured at 190° C. and 1 $sec^{-1}$ shear rate, may be from about 0.1 Pa-s to about 5,000 Pa-s and preferably from about 0.1 Pa-s to about 3,500 Pa-s. In some embodiments useful for printing or spraying, the compositions of the present invention may have shear viscosities ranging from about 1 to about 2000 Pa·s, preferably from about 5 to about 1000 Pa·s, and more preferably from about 10 to about 200 Pa·s, at 190° C. and 1 $s^{-1}$ shear rate.

In one embodiment, the composition of the present invention may have a normalized peak load of from about 100 to about 1000 Newtons/meter (N/m), preferably from about 200 to about 800 N/m, and more preferably from about 300 to about 700 N/m. In another embodiments, the composition of the present invention may have a peak strain of at least about 200%, preferably at least about 300%, and more preferably at least about 400%. In another embodiment, the composition of the present invention may have a room temperature normalized load at 200% strain of from about 40 to about 250 N/m, preferably from about 50 to about 200 N/m, and more preferably from about 60 to about 150 N/m. In another embodiment, the composition of the present invention may also have a force relaxation at 200% strain of less than about 50%, more preferably less than about 35%, and most preferably less than about 20%, at room temperature and 4 hours hold time.

Articles

The compositions of the present invention are suitable for use in elastic components of disposable articles, such as taped or fastened diapers, training pants, pull-on diapers, adult incontinence products, bandages, feminine protection products, wraps, heated wraps, wound dressings, surgical drapes, and the like. The elastic components may be portions of the absorbent article, such as the waistbands, leg cuffs, side panels, stretch ears, topsheet, and outer cover, that provide a body-conforming function, a restraint function, or other functions of the disposable article when it is worn. The compositions may also be used as stretchable woven or nonwoven fabric in durable articles, stretch garments including sports wear, swimwear, socks, undergarments, medical garments or devices, and the like. Other suitable uses include running shoe soles, hot melt glues, and any uses that benefit from flexible, stronger elastics.

The compositions of the present invention may also be used in paper or nonwoven products to increase the strength and/or wet strength. For example, the composition can be used to print a pattern or design on a substrate to increase the strength. If softness is desired, the composition can be printed on a middle layer of a substrate to increase strength but keep softness. Other functional benefits include printing on a substrate to increase the scrubbing or abrasive properties. The composition may also now be used to print intricate patterns. The printing and design flexibilities from these compositions enable a variety of uses that provide aesthetic and functional benefits.

The composition of the present invention can also be used to provide desired adhesive characteristics. The compositions can be used to make tack sheets, clean room wipes, tile adhesives pressure sensitive adhesives, caulking and other products such as label adhesives for bottles, boxes, computers, and other articles. It has been found that the composition is less adhesive once it crystallizes enabling the composition to release or peel off of a surface. This advantage enables materials to be utilized in rolls or other configurations where other adhesives are not suitable as they continue to adhere. The compositions of the present invention may also be utilized to improve process reliability enabling less down time.

Test Methods

A. Differential Scanning Calorimetry (DSC)

DSC is a well known method for thermal measurements. This method is capable of determining the temperature ranges at which the phase changes of materials occur. Here, the phase change temperatures are useful in selecting the phase change solvents and the processing oil and correlating with the processability and mechanical properties of the elastomeric compositions containing them.

The measurements were performed using a Model 822 DSC from Mettler, Columbus, Ohio or a System 7 DSC from Perkin-Elmer, Shelton, Conn. The instrument is interfaced with a computer for controlling the heating/cooling rates and other test parameters, and for collecting, calculating and reporting the data. The test procedure follows that of ASTM D3418 generally. The procedure is as follows:

(1) calibrate the instrument according to the manufacture's instructions;

(2) for the phase change solvent, a sample material (ca. 15 mg) is placed into aluminum pans, capped, crimped and placed into the instrument according to manufacturer's instructions; for the polystyrene homopolymer (MW=38,000 g/mol) in the presence of oil, a powdered or granular version of the polymer than can pass through a No. 24 sieve (USA Standard Testing Sieve, ASTM E-11) is employed. The powder is mixed in about a 1:1 oil to polymer ratio with the chosen processing oil. Approximately 0.5 gram of polystyrene and about 0.5 gram of oil are placed in a small vial and stirred with a spatula. After 24 hours, a sample material of the polystyrene/oil mixture (ca. 30 mg) is removed from the vial and placed into aluminum pans, capped, crimped and placed into the instrument according to manufacturer's instructions.

(3) if testing a new material, it may be necessary to perform one or more trial scans to determine an appropriate temperature range for the measurements, which should provide sufficient baseline before and after the observed transition; a typical temperature scan ranges from −50° C. to about 50° C. above the highest phase transition temperature of the sample being tested; for the phase change solvents of the present invention, a typical DSC scan ranges from −50° C. to 200° C.; for the glass transition temperature of polystyrene homopolymer in the presence of oil of the present invention, a typical DSC scan ranges from 25° C. to 200° C.

(4) program the instrument as follows: the sample temperature is set to the lower limit of desired test range; the temperature is held at the lower limit for 5 minutes and then it is increased at a rate of 10° C./min until reaching the upper limit; the temperature is held at the upper limit for 5 minutes and then the sample is cooled to the lower limit at 10° C./min; the temperature is held at the lower limit for 5 minutes and then the sample is heated at 10° C./min to the upper limit for a second heating scan;

(5) start the test and collect data simultaneously;

The results are analyzed using the procedure described in ASTM D 3418, Standard Test Method for Transition Temperatures of Polymers By Differential Scanning Calorimetry. The results are reported from the second heating cycle. For the phase change solvents of the present invention, the desired points on the curve (the onset temperature, the peak temperature, and the heat of phase transition) are determined using the procedure for a first-order transition stated in ASTM D 3418. For the polystyrene homopolymer in the presence of a processing oil of the present invention, the desired point on the curve (midpoint temperature of the glass transition temperature) is determined using the procedure for the glass transition stated in ASTM D 3418. In the present invention, the midpoint temperature of the glass transition temperature is designated as the glass transition temperature.

B. Pre-Strained Tensile Test

The properties determined by this method may correlate with the elastic forces a wearer feels from an elastic component incorporated into an absorbent product. The pre-straining step simulates the condition the elastic component experiences as the product is initially stretched in order to put the product on a wearer or to adjust the product to fit the wearer. Two methods are described, one to determine the peak load and the peak strain %, and one to determine the load at 200% strain and the unload at 30% strain. A new sample is used for each method.

A commercial tensile tester from Instron Engineering Corp., Canton, Mass. or SINTECH-MTS Systems Corporation, Eden Prairie, Minn. may be used for this test. The instrument is interfaced with a computer for controlling the test speed and other test parameters, and for collecting, calculating and reporting the data.

The sample is prepared by placing about 2 grams of the composition, which has been homogenized in chloroform and dried, between two TEFLON® sheets and this assembly is placed in a Carver Press. Metal shims with a thickness of 0.2 mm (10 mils) are placed between the TEFLON® sheets to control the thickness of the pressed film. The press is allowed to heat up to 215° C., and then 700 pounds (1540 kg) of pressure is applied for 5-10 seconds. The pressed film is immediately removed from the press and placed between two aluminum blocks (1" or 25.4 mm thick) to cool the film rapidly. The test samples (1" or 25.4 mm wide by 2" or 50.8 mm long) are cut from the pressed film. All surfaces of the sample shall be free of visible flaws, scratches or imperfections.

This test is done under standard laboratory conditions (i.e., at about 25° C. and about 50% relative humidity). The procedure is as follows:

(1) choose appropriate jaws and load cell for the test; the jaws should be wide enough to fit the sample, typically 1" wide jaws are used; the load cells is chosen so that the response from the sample tested will be between 25% and 75% of the capacity of the load cells or the load range used, typically a 50 lb load cell is used;

(2) calibrate the instrument according to the manufacture's instructions;

(3) set the gauge length at 1" (25.4 mm), and place the sample in the instrument according to the manufacture's instructions;

(4) stretch the sample at a constant speed of 10"/min (0.254 m/min) until it reaches 500% strain i.e., the gauge length is now 6" (15.24 cm); then return to the original gauge length at 10"/min (0.254 m/min); and at the end of this pre-straining cycle, start timing the experiment using a stop watch;

(5) reclamp the pre-strained sample to remove any slack and still maintain a 1" (25.4 mm) gauge length;

(6) at the three minute mark on the stop watch, start stretching the sample at a constant speed of 10"/min (0.254 m/min);

(7) a) the instrument records the forces versus distance during this cycle. The result is plotted as a load versus percent strain curve; the peak load and the peak strain can be obtained from the plot. The peak load is normalized and reported. The average result of three samples is reported. For this test, the peak load is normalized to 85 gsm as follows: the peak load from the plot is divided by the width of the sample, then multiplied by a normalizing factor, which is 85/(½*(actual weight of the sample/(width*gauge length) of sample in m$^2$)), or 85/(½(actual weight of the sample)/(6.47×10$^{-4}$)) if the sample dimension is measured in inches.

b) the sample is strained to 200% at a rate of 10"/min (0.254 m/min) and then returned to 0% strain at a rate of 10"/min (0.254 m/min). The instrument records the forces versus distance during this cycle. The result is plotted as a load versus percent strain curve. The load at 200% strain is recorded in Newtons/meter (N/m). The return to 0% strain is called an "unload" cycle. During the unload cycle, the load at 30% strain is recorded in Newtons/meter. The average result of three samples is reported. For this test, the load at 200% and the unload at 30% strain are normalized to 85 gsm as follows: the load from the plot is divided by the width of the sample, then multiplied by a normalizing factor, which is 85/(½*(actual weight of the sample/(width*gauge length) of sample in m$^2$)), or 85/(½(actual weight of the sample)/(6.47×10$^{-4}$)) if the sample dimension is measured in inches.

C. Force or Stress Relaxation Test

The property determined by this method may correlate with the forces a wearer experiences from an elastic component incorporated into a product. The first cycle is a pre-straining step that simulates the conditions the elastic component experiences as the product is initially stretched in order to put the product on a wearer or to adjust the product to fit the wearer. The second cycle measures the reduction in elastic forces (i.e., stress relaxation) resulting from the pre-straining step.

The instrument and the sample preparation are the same as Test Method B above. The pre-strain step (steps 1-6, as outlined below) is performed under standard laboratory conditions (i.e., at about 25° C. and about 50% relative humidity). Step 7 of the method is performed under environmental conditions of about 38° C. and about 50% relative humidity. The temperature is controlled using an Instron Engineering Corporation, 3119 Series Temperature Controlled Chamber Model 409. The procedure is as follows:

(1) choose appropriate jaws and load cell for the test; the jaws should be wide enough to fit the sample, typically 1"(25.4 mm) wide jaws are used; the load cells is chosen so that the response from the sample tested will be between 25% and 75% of the capacity of the load cells or the load range used, typically a 50 lb (22.7 kg) load cell is used;

(2) calibrate the instrument according to the manufacturer's instructions; set the gauge length at 1" (25.4 mm) and place the sample in the instrument according to the manufacturer's instructions;

(3) set the cross head speed at a constant speed of 10"/min (0.254 m/min);

(4) at standard laboratory conditions pre-strain the sample to 500% strain and immediately (i.e., without holding time) return to 0% strain; and at the end of this pre-straining cycle, start timing the experiment using a stop watch.

(5) remove sample from the jaws and wait 15 minutes. The sample is resting at standard laboratory conditions. At the beginning of the 15 minute period, program the environmental chamber to about 38° C. and close the chamber door.

(6) at the fifteen minute mark on the stop watch, open environmental chamber door and reclamp the pre-strained sample. Remove any slack and maintain a 1" (2.54 cm) gauge length. Close the environmental chamber door. Start the sustained load stress relaxation test and collect data simultaneously. The sustained load stress relaxation test has the following steps:

a) go to 200% strain at a rate of 10"/min (0.254 m/min);
b) hold position for time=4 hours;
c) go to 0% strain at a rate of 10"/min (0.254 m/min); and
d) calculate the stress relaxation at 200% strain as the % loss between the initial load and the load at time, t of step 7(b) as follows:

$$\% \text{ Force Relaxation at time, } t = \frac{[(\text{initial load}) - (\text{load at time, } t)]}{(\text{initial load})} \times 100$$

(7) The average result of three samples is reported. The load at 200% strain of step 7(a) is normalized to 85 gsm as follows: the load at 200% strain from the plot is divided by the width of the sample, then multiplied by a normalizing factor, which is 85/(½* (actual weight of the sample/(width*gauge length) of sample in m$^2$)), or 85/(½*(actual weight of the sample)/(6.47×10$^{-4}$)) if the sample dimension is measured in inches.

D. Molecular Weight Determination

Number-average molecular weights are estimated by analysis of the NMR (Nuclear Magnetic Resonance) spectra of the compounds. Methyl end groups are quantified via their peak at 1 ppm while the aromatic content is quantified by their peak at approximately 7-8 ppm. Methylene esters are quantified via their peak at approximately 4-4.5 ppm and aliphatic methylenes are quantified via their peaks from 1.5-2.5 ppm. From these quantified values a product structure is determined and the molecular weight is calculated.

E. Shear Viscosity Test

Samples are prepared by the hot press method described in Test Method B, except that about 5 grams of homogenized composition and 1.2 mm (60 mils) thick metal shims are used.

Shear viscosity of the sample can be measured using the ARES Polymer Melt Rheometer (manufactured by Rheometrics, Piscataway, N.J.) in the parallel plate mode. The sample handling and instrument operation generally follow the operating manual provided by the manufacturer, except for the specific testing conditions described herein. In this test, parallel plates that are 25 mm in diameter and have 1 mm gap between them are used and the instrument is equipped with a heated chamber to control the test temperature.

The hot pressed sample is loaded into the instrument, which is preheated to a temperature of about 100° C. Then the parallel plates are pressed together leaving a gap distance of 1 mm between them. After a sufficient time to allow the sample to equilibrate, excess sample is removed. The shear viscosity $\eta^*$ is measured at 1 s$^{-1}$ oscillating at 5% strain. The instrument is operated in a temperature scan mode, wherein the temperature is ramped up at 5° C./min over the range from 100° C. to at least 50° C. above the highest phase transition temperature.

Some samples may require higher loading temperature in order to fill the gap between the parallel plates. The loading temperature may be adjusted higher as needed and the temperature scan will start at the higher temperature.

Figure 2:
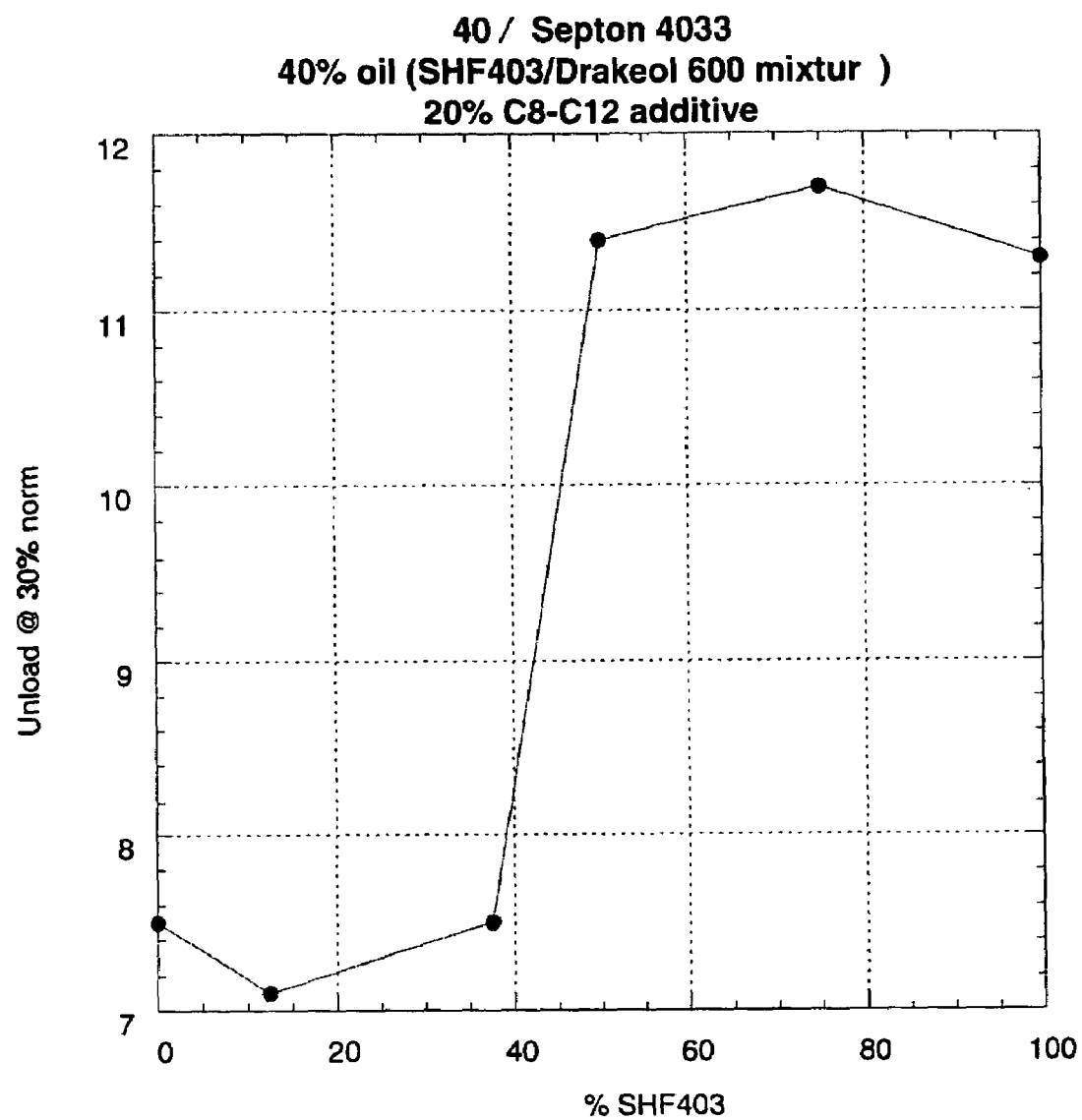
FIG. 2 is a plot depicting the tensile behavior (exemplified by the value of Unload @ 30% strain) of example elastomer formulations containing elastomer, phase change solvent, and synthetic/mineral oil mixtures.

FIG. 1 shows the glass transition temperatures for polystyrene homopolymer in the presence of an oil composition. The results were obtained from employing polystyrene with MW=38,000 g/mol under the test conditions described below. The molecular weights and chemical structure play a large role in determining the extent of Tg reduction for polystyrene. As shown in FIG. 1, the Tg of 100% mineral oil (0% SHF 401 (synthetic oil)) is approximately 77° C. The Tg of 100% SHF 401 (0% mineral oil) is approximately 99° C. The Tg is greater than about 85° C. when greater than about 35% SHF 401 is present. The Tg continues to increase as the amount of synthetic oil, SHF 401, increases. FIG. 2 depicts the improvements in tensile strength (here embodied in Unload @ 30% strain) with the presence of synthetic oil in the elastomeric formulation. As shown, there is a significant increase in tensile strength when greater than about 45% or more preferably greater than about 50% of synthetic oil (SHF 401) is included in the processing oil composition.

EXAMPLES

Examples 1-4

An elastomeric composition is prepared by mixing and stirring the phase change solvent described in Example 1 of U.S. patent application Ser. No. 10/429,513 (Case 9005M), filed May 5, 2003. A phase change solvent having the general formula (I) is prepared by combining 260 grams (2 moles) of octanol with 404 grams (2 moles) of terephthaloyl chloride and 202 grams (1 mole) of 1,12-dodecanediol in 1500 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting reaction mixture is poured into a large quantity of methanol to precipitate the product. The precipitant is collected over a filter, washed with 500 ml of methanol 3 times and dried at 45° C. in a vacuum oven for 20 hours. The resulting product has a number-average molecular weight of about 720 and an AA ratio of 2.3. The phase change solvent is stirred until the sample appears to be homogeneous. The synthetic processing oil, SHF-401 (available from Exxon-Mobil Company, Houston, Tex.) is then added to the mixture and stirred at room temperature for 16 hours to form an elastomeric composition.

Alternative, the composition is prepared by mixing all the components in chloroform (5 grams total weight of the composition in 45 grams of chloroform) and stirring for 2 hours or until the mixture appears homogeneous. The mixture is then poured into a TEFLON® dish and let dry at room temperature overnight. The mixture and the TEFLON® dish are placed in a vacuum oven for an hour at 60° C.

The above blending method is merely exemplary. Other conventional blending methods using batch mixers, screw extruders, and the like, may also be used.

| Example | 1 | 2 | 3 | 4 |
|---|---|---|---|---|
| Viscosity, Pa-s @ 190° C. | 25 | 180 | 29 | 54 |
| Unload @ 30%, N/m | 7.5 | 12.3 | 8.4 | 11.4 |
| Peak Load, N/m | 194 | 414 | 250 | 383 |

Control-Example 1

A composition is prepared to contain 40% Septon 4033 (from Kuraray America, Inc., New York, N.Y.), 40% Drakeol 600 mineral oil (Penreco Corp.), and 20% of phase change solvent with C8,C12 terephthtalate. All materials co-dissolved in chloroform. The solution is then dried slowly under ambient conditions. The data for the control, the processing oil is mineral oil (100% natural oil), show that the viscosity remains very high and the tensile properties for unload and peak load are also low.

Example 2

A composition is prepared to contain 40% Septon 4033 (Kuraray Corp.), 40% SHF 401 polyalpha olefin (Exxon-Mobil Company), and 20% of phase change solvent with C8,C12 terephthtalate. All materials co-dissolved in chloroform. The solution is then dried slowly under ambient conditions. The data for this preferred composition of the present invention, process oil is polyalpha olefin (100% synthetic oil), show that the viscosity is very low and the tensile properties for unload and peak load are also in desired ranges.

Control-Example 3

A composition is prepared to contain 40% Septon 4033 (Kuraray Corp.), 30% Drakeol 600 mineral oil (Penreco Corp.), 10% SHF 401 polyalpha olefin (Exxon-Mobil Company), and 20% of phase change solvent with C8,C12 terephthtalate. All materials co-dissolved in chloroform. The solution is then dried slowly under ambient conditions. The data for this control (processing oil composition contains 25% synthetic oil (polyalpha olefin)), show that the viscosity remains high and the tensile properties for unload and peak low are also lower than desired.

Example 4

A composition is prepared to contain 40% Septon 4033 (Kuraray Corp.), 20% Drakeol 600 mineral oil (Penreco Corp.), 20% SHF 401 polyalpha olefin (Exxon-Mobil Company) and 20% of phase change solvent with C8,C12 terephthtalate. All materials co-dissolved in chloroform. The solution is then dried slowly under ambient conditions. The data for this composition of the present invention (process oil composition contains 50% synthetic oil (polyalpha olefin)), show that the viscosity is decreased and the tensile properties for unload and peak load are increased.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A composition comprising:
   a) from about 1 to about 98 wt % a thermoplastic elastomer, which is a block copolymer having at least one soft block and at least one hard block;
   b) from about 1 to about 70 wt % a phase change solvent having the general formula:

R'-Py-(Q-Px)n-Q-Py-R; (I)

R'-Py-(Q-Px)n-R; (II)

R'-(Q-Px)n-R; (III)

R'-(Q-Px)n-1-Q-Py-R; (IV)

R'-(Q-Px)n-Q-R; or (V)

a mixture thereof;
   wherein Q is an unsubstituted difunctional aromatic moiety; P is CH2; R and R' are the same or different and are independently selected from H, CH3, COOH, CONHR1, CONR1R2, NHR3, NR3R4, hydroxy, or C1-C30 alkoxy; wherein R1, R2, R3 and R4 are the same or different and are independently selected from H or linear or branched alkyl from C1-C30; x is an integer from 1 to 30; y is an integer from 1 to 30; and n is an integer from 3 to 7; and
   c) from about 1 to about 70 wt % of a processing oil selected from the group consisting of poly (alpha olefins), olefinic oligomers, mineral oils, paraffinic oils, isoparaffinic oils, naphthenic oils, petrolatum, waxes, or mixtures thereof producing a glass transition temperature of greater than 85° C. for a polystyrene homopolymer;
   wherein the phase change solvent has a phase change in a temperature range from about 40° C. to about 250° C.

2. The composition of claim 1 wherein the processing oil producing a glass transition temperature of greater than about 87° C. for a polystyrene homopolymer.

3. The composition of claim 1 wherein the processing oil producing a glass transition temperature of greater than about 90° C. for a polystyrene homopolymer.

4. The composition of claim 1 wherein the synthetic processing oil is a poly (alpha olefin).

5. The composition of claim 4 wherein the poly(alpha olefin) is selected from the group consisting of polydodecenes, polydecenes, polyoctenes, polybutylenes, polybutenes, and mixtures thereof.

6. The composition of claim 4 wherein the poly(alpha olefin) is selected from the group consisting of poly(1-decene), poly(1-dodecene), poly(1-octene), and mixtures thereof.

7. The composition of claim 1 wherein the processing oil is a mixture of a synthetic oil and a natural oil.

8. The composition of claim 7 wherein the synthetic oil comprises at least about 40% of the processing oil mixture.

9. The composition of claim 1 wherein the processing oil has a molecular weight in the range of from about 500 to about 3000 g/mol.

10. The composition of claim 1 additionally comprising from about 1 to about 50 wt % a thermoplastic polymer.

11. The composition of claim 1 wherein the composition has a shear viscosity of about 0.1 to about 3000 Pa·s at 190° C. and 1 sec−1.

12. A composition comprising:
    a) from about 1 to about 99 wt % a thermoplastic elastomer, which is a block copolymer having at least one soft block and at least one hard block;
    b) from about 1 to about 70 wt % a phase change solvent having the general formula:

R'-Py-(Q-Px)n-Q-Py-R; (I)

R'-Py-(Q-Px)n--R; (II)

R'-(Q-Px)n-R; (III)

R'-(Q-Px)n-1-Q-Py-R; (IV)

R'-(Q-Px)n-Q-R; or (V)

a mixture thereof;
    wherein Q is an unsubstituted difunctional aromatic moiety; P is CH2; R and R' are the same or different and are independently selected from H, CH3, COOH, CONHR1, CONR1R2, NHR3, NR3R4, hydroxy, or C1-C30 alkoxy; wherein R1, R2, R3 and R4 are the same or different and are independently selected from H or linear or branched alkyl from C1-C30; x is an integer from 1 to 30; y is an integer from 1 to 30; and n is an integer from 3 to 7; and
    c) from about 1 to about 70 wt % of a processing oil composition comprising a synthetic oil and a natural oil and producing a glass transition temperature of greater than about 85° C. for a polystyrene homopolymer;
    wherein the phase change solvent has a phase change in a temperature range from about 40° C. to about 250° C.

13. A method of lowering the viscosity and improving the processability of a thermoplastic elastomer, the method comprising the step of:
    blending from about 1 to about 99 wt % of the thermoplastic elastomer, which is a block copolymer having at least soft block and at least one hard block, from about 1 to about 70 wt % of a phase change solvent having the general formula (I)-(V) of claim 1, or a mixture thereof, and from about 1 to about 70 wt % of a processing oil producing a glass transition temperature of greater than about 85° C. for a polystyrene homopolymer to form an elastomer composition;
    wherein the shear viscosity of the elastomeric composition is lower than the shear viscosity of the thermoplastic elastomer when measured at 190° C. and 1 sec−1.

14. The method of claim 13 wherein the elastomeric composition has a shear viscosity of about 0.1 to about 3000 Pa·s at 190° C. and 1 sec−1.

15. The method of claim 13 wherein the processing oil has a molecular weight in the range of from about 500 to about 3000 g/mol.

16. The method of claim 13 wherein the processing oil comprises 50% of a mineral oil and 50% of a synthetic oil.

17. The method of claim 16 wherein the synthetic oil is a poly (alpha olefin).

18. The composition of claim 1 additionally comprising from about 0.1 to about 50 wt % a nucleating agent.

19. The method of claim 13 further comprising blending one or more additional ingredient with the thermoplastic elastomer, the phase change solvent, and processing oil, wherein the additional ingredient is selected from the group consisting of:

from about 0.1 to about 50 wt % of a nucleating agent;
from about ito about 50 wt % of a thermoplastic polymer;
and mixtures thereof.

* * * * *

UNITED STATES PATENT AND TRADEMARK OFFICE
CERTIFICATE OF CORRECTION

PATENT NO. : 7,468,411 B2  
APPLICATION NO. : 10/769344  
DATED : December 23, 2008  
INVENTOR(S) : Steven Daryl Smith et al.

Page 1 of 1

It is certified that error appears in the above-identified patent and that said Letters Patent is hereby corrected as shown below:

Figure 2
Line 2 of the text at the top of the page, delete "mixtur )" and insert -- mixture) --.

Column 6
Lines 2-3, delete "Theological" and insert -- rheological --.

Column 18, Claim 19
Line 2, delete "ito" and insert -- 1 to --.

Signed and Sealed this
Fourteenth Day of June, 2011

David J. Kappos
*Director of the United States Patent and Trademark Office*